(12) United States Patent
Marquard, II et al.

(10) Patent No.: US 6,484,720 B1
(45) Date of Patent: Nov. 26, 2002

(54) FIVE SPRING REGULATOR

(75) Inventors: David J. Marquard, II, Avon Lake, OH (US); Ronald J. Johnson, Wellington, OH (US)

(73) Assignee: Applied Marketing, Inc., North Olmsted, OH (US)

( * ) Notice: Subject to any disclaimer, the term of this patent is extended or adjusted under 35 U.S.C. 154(b) by 97 days.

(21) Appl. No.: 09/692,588

(22) Filed: Oct. 20, 2000

(51) Int. Cl.<sup>7</sup> ................................................ A62B 9/02
(52) U.S. Cl. ................... 128/205.24; 137/535
(58) Field of Search .................... 137/116.5, 505.18, 137/505.42, 494, 625.5, 113, 102, 535–543.23; 128/200.24, 204.18, 204.21, 204.25, 204.26, 205.14, 205.24, 207.12, 207.16

(56) References Cited

U.S. PATENT DOCUMENTS

| | | | | |
|---|---|---|---|---|
| 4,037,594 A | * | 7/1977 | Riegel et al. | 137/505.18 |
| 5,372,159 A | * | 12/1994 | Ziegelmeyer et al. | 137/505.14 |
| 5,542,417 A | * | 8/1996 | Ottestad | 128/205.24 |
| 6,116,242 A | * | 9/2000 | Frye et al. | 128/205.24 |
| 6,189,531 B1 | * | 2/2001 | Tatarek | 128/205.24 |

OTHER PUBLICATIONS

Spence Engineering Company, Inc. catalog pp. (2) describing a Type J Control Valve, printed in the U.S.A. approximately 1997.

Precision Medical advertising, instructions and packaging for a dial regulator describing the Oxygen Therapy Regulator 1600 Series printed in the U.S.A. in Nov. 1996.

* cited by examiner

Primary Examiner—Glenn K. Dawson
(74) Attorney, Agent, or Firm—Fay, Sharpe, Fagan, Minnich & McKee

(57) ABSTRACT

An oxygen gas therapy regulator is provided which is small in size and has particularly uniform output characteristics. The regulator uses five springs evenly spaced around a circle concentric with the axis of the regulator piston thereby providing uniform output characteristics.

10 Claims, 2 Drawing Sheets

FIVE SPRING REGULATOR

BACKGROUND OF THE INVESTIGATION

This invention relates to gas regulators and more particularly to an oxygen gas regulator adapted to dispense therapeutic oxygen at a controlled pressure.

Oxygen gas is used widely in treating human medical conditions. Oxygen gas is dispensed in hospitals, emergency response vehicles and other locations when dealing with critical situations. Oxygen gas is also dispensed in treating chronic conditions such as emphysema. Oxygen gas must be dispensed at a controlled pressure and flow rate in these applications. Moreover, the oxygen gas is often dispensed in mobile environments such as emergency vehicles, the home or from portable dispensers used by persons with chronic conditions. The dispensers must be rugged, light and easy to use. One way of addressing this need is the dispensing of oxygen gas from containers, sometimes referred to as tanks or bottles, which are relatively small and hold oxygen gas under high pressure, e.g., 2000–3000 psi. The oxygen gas containers are provided with an outlet of conventional design and an on/off valve. A regulator is applied to the outlet, the tank valve opened and oxygen provided through the regulator to a regulator output. The regulator provides oxygen at a desired pressure and flow rate at its output. Some such regulators have a variable outlet flow rate.

The described regulators work reasonably well. However, improvements are desired.

Oxygen therapy is used by a wide variety of people and therefore oxygen regulators must be easy to use and understand. Oxygen gas regulators are used in mobile environments and therefore subject to mechanical shock, unintended impact and the like. Oxygen regulators must therefore be robust.

It is desirable that oxygen regulators have a consistent repeatable output pressure for their intended flow range. If a physician prescribes a particular oxygen supplementation level, such a prescription can only be followed if the person setting up the oxygen supply can rely upon the stated output parameters of a regulator.

Oxygen regulators need to be inexpensive to manufacture and easy to maintain.

Prior art regulators which are appropriate for use in the medical dispensing of oxygen gas, especially mobile dispensing, have a relatively broad variation of output parameters from one regulator to the next. Some prior art regulators are big, heavy and subject to damage. Other prior art regulators are expensive. Other prior art regulators require maintenance or adjustment which are beyond the capacity of many users.

SUMMARY OF THE INVENTION

The above described requirements are achieved and the problems overcome in the present invention in which a small oxygen gas regulator is provided with an array of five biasing springs rather than a single biasing spring.

In accordance with the present invention, there is provided an oxygen gas regulator comprising a regulator body having an inlet receiving oxygen from an oxygen tank, an upper chamber receiving gas from the gas inlet, a lower chamber, a gas outlet receiving gas from the lower chamber, a passage from the upper chamber to the lower chamber, a movable piston having a low pressure surface exposed in the lower chamber and an atmospheric surface exposed to atmospheric pressure, an orifice controlling flow of gas into the upper chamber, the orifice being controlled by the piston, and five biasing springs urging the piston toward the lower chamber.

Yet further in accordance with the invention, the five biasing springs are evenly spaced around a circle which is concentric with the axis of the piston.

Still further in accordance with the invention, the five biasing springs are received in pockets in a support which is immovable with respect to the valve body.

Still further in accordance with the invention, the five biasing springs are small coil springs having identical nominal spring rates.

It is the principal object of the present invention to provide an oxygen gas regulator which is inexpensive to manufacture, easy to maintain and provides more uniform output parameters than conventional regulators.

It is yet another object of the present invention to provide a gas regulator in which variations in output parameters due to variations in part parameters, e.g., spring characteristics, is minimized.

It is yet another object of the present invention to provide an oxygen gas regulator which maintains output characteristics over its design range.

It is still another object of the present invention to provide an oxygen gas regulator which delivers oxygen gas at the desired pressure and flow rate over a broad range of gas input pressures.

It is yet another object of the present invention to provide an oxygen gas regulator requiring only minimal maintenance.

It is still another object of the present invention to provide an oxygen gas regulator requiring only minimal field calibration.

It is still another object of the present invention to provide an oxygen gas regulator which is robust, small, easy to use, and lightweight.

These and other objects of the present invention will become apparent to those skilled in the art from the following description taken in conjunction with the accompanying drawings wherein.

PREFERRED EMBODIMENT

Figure 1:
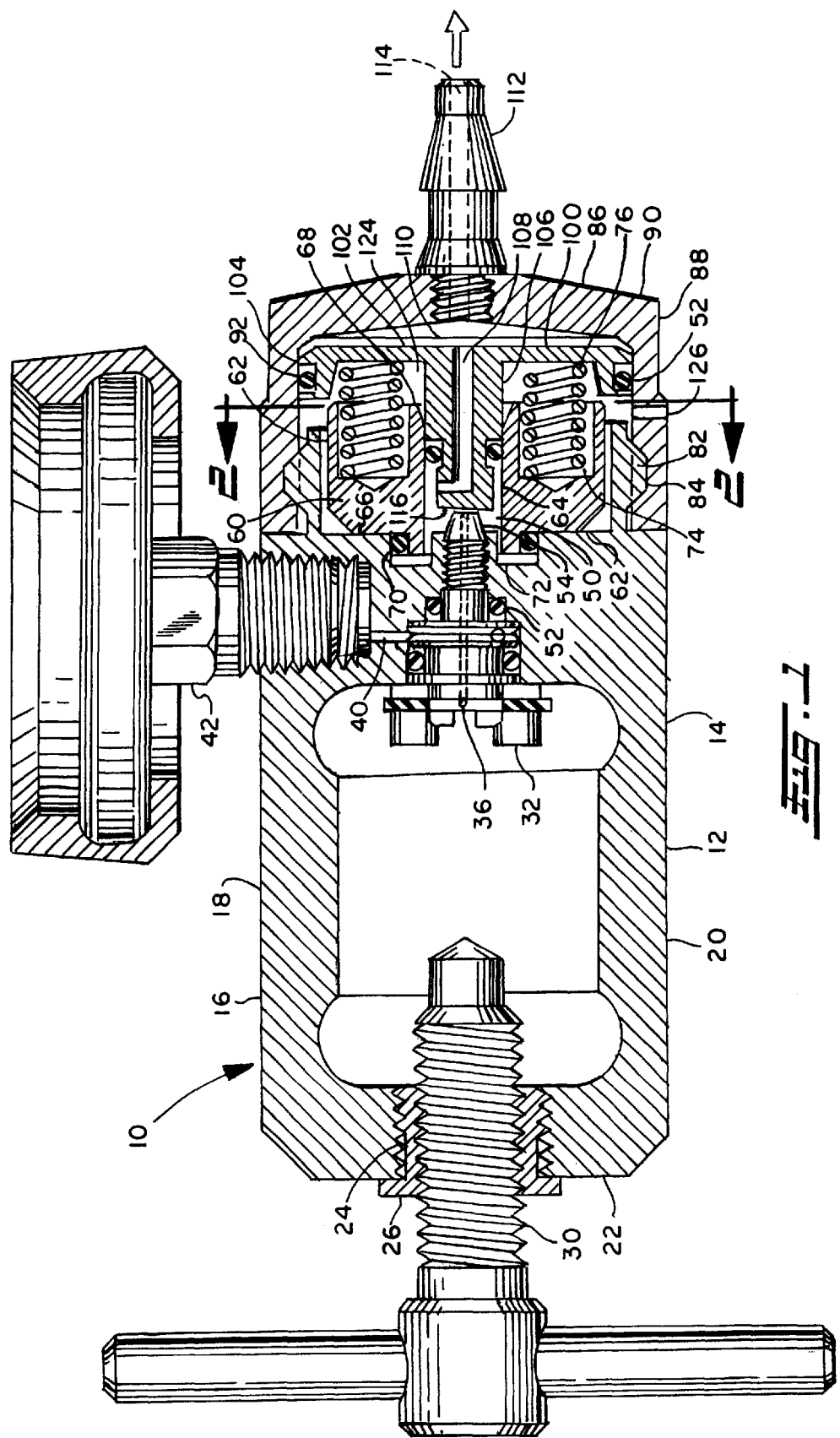
FIG. 1 shows the regulator of the present invention in partial longitudinal cross section.

Referring now to the drawings wherein the showings are for the purposes of illustrating a preferred embodiment of the invention and not for the purpose of limiting same, the Figures show a gas regulator 10 having a regulator body 12. The regulator body 12 has a cylindrical portion 14 and a yoke portion 16 extending from the cylindrical portion 14. The yoke portion 16 is conventional and has two parallel legs 18, 20 joining the cylindrical portion 14. The ends of the legs 18, 20 away from the cylindrical portion are joined by a bridge 22 having a hole 24 at its center. The hole can be threaded or, as shown in the preferred embodiment, a threaded bushing 26 can be placed in the hole 24. A threaded screw clamp 30 passes through the bushing 26. In the preferred embodiment, the screw clamp 30 has a T-shape making it easy to turn. Other shapes are acceptable.

On the cylindrical portion 14 of the regulator body 12, a seat insert 32 is provided opposite the screw clamp 30. In use, the screw clamp 30 is backed out, the regulator is applied to an oxygen tank with the outlet of the tank facing the seat insert 32 and the screw clamp tightened against the opposite side of the tank outlet portion. Oxygen tank outlet portions are conventional in design and the portions of the regulator just described which mate with the tank outlet are also conventional.

The seat insert 32 is positioned in a recess on the axis of the regulator body. The seat insert 32 mates with the gas outlet on an oxygen tank. A filter (not shown) is positioned in the opening. Gas flows through the filter into a channel 36 along the axial center of the seat insert 32. A radial branch (not shown) of the channel 36 allows high pressure gas to flow to a gage channel 40 in the cylindrical portion 14 of the regulator body 12. The gage channel 40 allows a small flow of gas to a gage 42 which is conventional and which indicates the oxygen pressure in the tank to which the regulator is fixed. Passages, orifices and the like are shown much larger than actual size for purposes of clarity.

The main flow of gas through the channel 36 continues through the seat insert 32 along its axis into an upper chamber 50. Thus, high pressure gas can flow from the oxygen tank, through the filter, through the channel 36, into the upper chamber 50. The seat insert 32 is a machined element fabricated from brass or the like. O-rings 52 and other seals are provided to maintain gas tight integrity as is conventional.

The seat insert 32 is provided with a conical surface 54 at its end which penetrates into the upper chamber 50. The gas passage channel 36 terminates at the tip of the conical surface 54, truncating it perpendicular to its axis. The seat insert 32 is fixed to the regulator body 12. The truncated conical surface 54 and the channel 36 end will not move with respect to the regulator body 12.

The upper chamber 50 is generally cylindrical. Its side wall is defined by a spring support 60 which has a generally cylindrical outer wall 62, a cylindrical axial central opening 64, a generally flat top side 66, and a generally flat bottom side 68. A top flange 70 is received in a mating toroidal recess 72 in the regulator body cylindrical portion 14. An O-ring 52 is provided to seal the upper chamber 50 and prevent leakage of gas between the spring support 60 and the regulator body cylindrical portion 14. The spring support 60 rests against the regulator body cylindrical portion 14. There is no need for movement at this point once the regulator is assembled.

Figure 2:
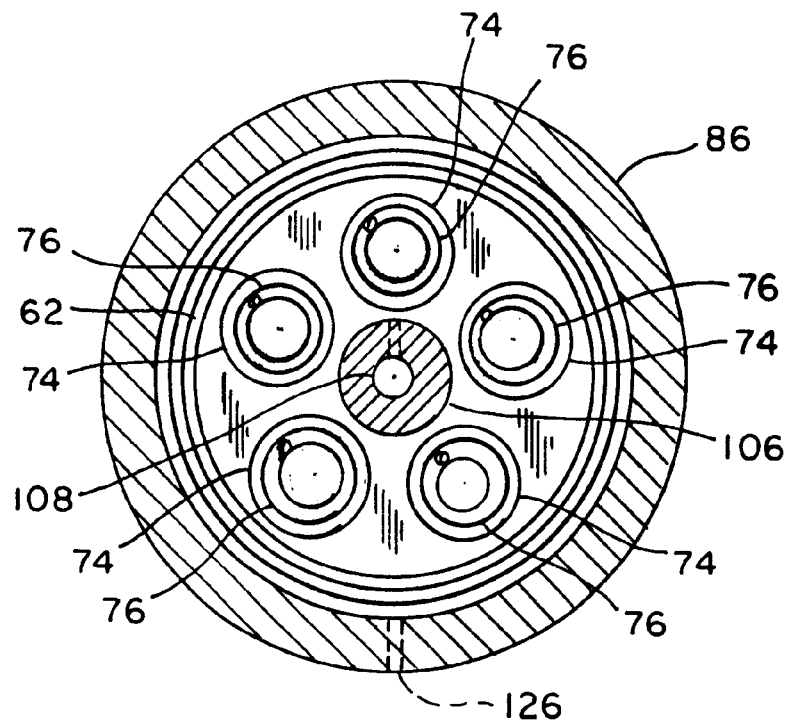
FIG. 2 is a cross section taken along line 2—2 of FIG. 1 showing the arrangement of biasing springs in the present invention; and, FIG. 3 is an enlarged partial cross section of the seat insert and piston top.
Figure 3:
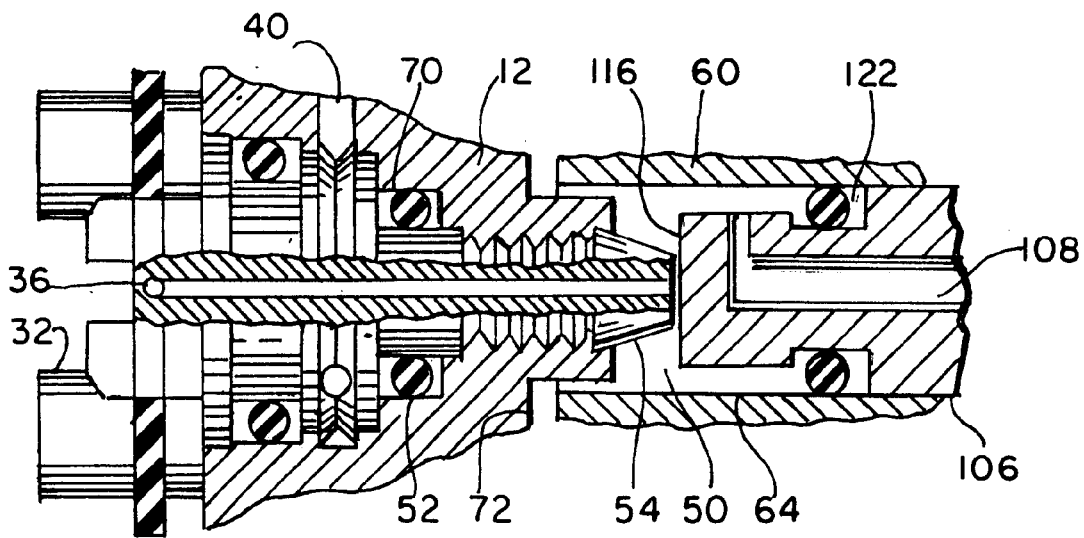

The spring support 60 bottom side 68 is provided with five recesses 74. The recesses 74 are evenly spaced around a circle which is concentric with the spring support central opening 64. This arrangement is best seen in FIG. 2. Five springs 76 are accommodated in the recesses 74. The recesses are sufficiently deep so that the springs will be supported projecting coaxially with the axes of the recesses 74 with their outboard ends extending well beyond the spring support 60 bottom side 68.

The regulator body 12 has a cylindrical extension 82 which extends from the bottom of the cylindrical portion 14 and surrounds a portion of the spring support 60. The external surface of the cylindrical extension 82 is provided with threads 84. A cup shaped bonnet 86 has a cylindrical side wall 88 and a slightly conical bottom wall 90. The cylindrical side wall has internal thread which mate with the threads 84 on the regulator body extension 82. The bonnet is thereby held in place on the cylindrical body. The bonnet cylindrical side wall 88 has a cylindrical internal surface 92 near the conical bottom wall 90.

A piston 100 is disposed within the bonnet 86. The piston 100 is comprised of a disk shaped bottom 102 with a cylindrical outer flange 104 and a cylindrical central barrel portion 106 concentric with the outer flange 104 and the disk shaped bottom 102. A central passage 108 extends from the center of the bottom of the piston upwardly along its axis to a point in the upper chamber 50 where the passage turns and becomes radial. The passage provides gas communication between the upper chamber 50 and a lower chamber 110. The passage 108 is shown much larger than actual size for clarity. The passage 108 has a diameter significantly larger than the diameter of the channel 36 through the seat insert 32. An O-ring 52 is disposed in a recess in the cylindrical outer flange 104 and forms a seal between the cylindrical outer flange 104 and the bonnet cylindrical internal surface 92. This allows the piston to move axially within the bonnet 86 while maintaining a seal between the piston 100 and the bonnet 86. The piston disk shaped bottom 102, the bonnet cylindrical side wall 88 and the bonnet conical bottom wall 90 define the lower chamber 110. A regulator output barb 112 is positioned at the center of the bonnet conical bottom wall 90. The barb has a large diameter output passage 114 which allows gas to flow from the lower chamber 110 through the barb 112 to an oxygen output hose (not shown).

The piston central barrel portion 106 extends upwardly toward the seat insert 32 through the central opening 64 in the spring support 60. The piston barrel portion 106 has a recess 122 accommodating an O-ring 52 which seals against the spring support central opening 64. The portion of the piston barrel portion 106 above the O-ring 52 is within the high pressure chamber 50 and the O-ring 52 provides the seal isolating the high pressure chamber 50.

The piston central barrel portion 106 has a flat top surface 116 directly adjacent the conical surface 54 of the seat insert 32. The tip of the conical surface 34 is the outlet of high pressure gas channel 36. The area around the tip of the conical portion 54 directly adjacent to and close to the flat surface 116 forms an orifice which is variable with the movement of the piston 100. This variable orifice controls the flow of gas into the upper chamber 50 through the channel 36. If the piston moves toward conical surface 54, the orifice is made smaller and the flow of gas is restricted. If the piston 100 moves away from the conical surface 54, the orifice is made larger and the flow of gas into the upper chamber 50 increases. The movement is very small.

The portion of the regulator between spring support 60 and the piston 100 is an atmospheric pressure chamber 124. The atmospheric pressure chamber 124 is sealed from the lower chamber by the O-ring 52 in the piston cylindrical outer flange. The atmospheric pressure chamber is sealed from the upper chamber by the O-ring in the recess 122 and the O-ring in the top flange 70 of the spring support 60. The atmospheric pressure chamber 124 is vented to atmosphere through a port 126 through the bonnet 86.

The passage 108 through the piston has a diameter larger than the diameter of the channel 36 admitting gas into the upper chamber. The upper chamber 50 and lower chamber 110 are therefore at substantially the same pressure.

The forces acting on the piston 100 include the force of gas pressure acting against the top of the piston central barrel portion 106. This is substantially cancelled by the gas pressure acting against the bottom of the piston under the central barrel portion. Atmospheric pressure acting against the area of the disk comprising the entire area of the disk minus the area of the central barrel portion acts to push the piston downwardly (to the right in FIG. 1). The spring force exerted by the five springs 76 acting against the piston adds to the force exerted by the atmospheric pressure chamber. Opposing these forces is the force applied by the gas contained in the lower chamber 110 acting against the bottom 102 of the piston 100. These forces are balanced when the regulator is in the steady state with the force exerted by the gas in the lower chamber balancing the forces exerted by the gas in the atmospheric chamber and the spring force exerted against the piston. Of course, the function of the regulator is to maintain a constant pressure in the lower chamber 110. This is accomplished by moving the piston thus changing the orifice allowing gas into the upper chamber 50. Higher pressure in the lower chamber 110 pushes the piston 100 up and decreases the flow of oxygen gas through the tip of the conical surface 54 thereby lowering the pressure in the upper chamber and lower chamber thereby restoring appropriate pressure in response to changes in demand and the like.

This regulating function is performed more uniformly in the present invention because of the use of five springs. Springs made to the same specification will vary in spring force and other characteristics within a certain range. These variations will cause variations in regulators. Variations in spring force of a certain percentage from spring to spring will cause variations in regulator output of a certain percentage. In the present invention, five springs are used. With the use of five springs, variations from nominal ratings will have a tendency to cancel out. Some of the five springs will be slightly stronger than average and some will be slightly weaker. The total spring force will be closer to the specification in almost all situations. Thus, variations from one regulator to the next are minimized.

The use of five springs evenly spaced around a circle concentric with the axis of the piston also helps compensate for variations in individual springs. A spring that has a particularly low spring constant, in almost all circumstances, will be flanked by two springs having stronger spring constants. Moreover, the force acting on the piston at the point of the weakest spring will not result in misalignment of the piston because no matter where one draws a diameter there are always at least two springs on each side of the diameter. The piston is less likely to bind and will react to pressure differences more readily.

The invention has been described with reference to a preferred embodiment. Obviously, modifications and alterations will occur to others upon a reading and understanding of the specification and it is intended to include such modifications and alterations insofar as they come within the scope of the appended claims or the equivalents thereof.

Having thus described the invention, it is so claimed:

1. An oxygen gas regulator for medical use comprising:
   a regulator body having a gas inlet admitting gas at high pressure;
   an upper chamber receiving gas from said gas inlet;
   a lower chamber;
   a gas outlet receiving gas from said lower chamber;
   a passage from said upper chamber to said lower chamber;
   an atmospheric pressure chamber;
   a movable piston having a bottom surface exposed in said lower chamber and a top surface exposed in said atmospheric pressure chamber;
   a variable orifice controlling flow of gas through said gas inlet, said variable orifice being controlled by said piston; and,
   five biasing springs urging said piston toward said lower chamber.

2. The regulator of claim 1, wherein said piston has a central axis and said springs are received in recesses evenly spaced about a circle concentric with said axis.

3. The regulator of claim 2, wherein said recesses are cylindrical pockets.

4. The regulator of claim 3, wherein said cylindrical pockets are in a spring support.

5. The regulator of claim 4, wherein said regulator body is generally cylindrical and has an axis and said piston axis is coaxial with said regulator axis.

6. An oxygen gas regulator for medicinal use comprising:
   a regulator body having a gas inlet admitting gas to an upper pressure chamber;
   a lower chamber communicating with said upper chamber having a low pressure gas outlet;
   a piston exposed to said lower chamber, said piston controlling an orifice controlling the flow of gas into said upper chamber; and,
   five biasing springs urging said piston toward said lower chamber.

7. The regulator of claim 6, wherein said orifice is at the junction of the gas inlet and the upper chamber.

8. The regulator of claim 7, wherein said orifice is formed by the center of said piston and said gas inlet.

9. The regulator of claim 8, wherein said piston has a central axis and said springs are received in cylindrical pockets evenly spaced about a circle concentric with said axis.

10. The regulator of claim 9, wherein said cylindrical pockets are in a spring support.

\* \* \* \* \*

UNITED STATES PATENT AND TRADEMARK OFFICE
CERTIFICATE OF CORRECTION

PATENT NO.   : 6,484,720 B1  Page 1 of 1
DATED        : November 26, 2002
INVENTOR(S)  : David J. Marquard, II and Ronald J. Johnston It is certified that error appears in the above-identified patent and that said Letters Patent is hereby corrected as shown below:

<u>Title page,</u>
Item [75], delete the inventor name "Ronald J. Johnson" and insert
-- Ronald J. Johnston --.

Signed and Sealed this

Twenty-fifth Day of February, 2003

JAMES E. ROGAN
*Director of the United States Patent and Trademark Office*

(12) EX PARTE REEXAMINATION CERTIFICATE (5303rd)
United States Patent
Marquard, II et al.

(10) Number: US 6,484,720 C1
(45) Certificate Issued: Mar. 14, 2006

(54) FIVE SPRING REGULATOR

(75) Inventors: David J. Marquard, II, Avon Lake, OH (US); Ronald J. Johnston, Wellington, OH (US)

(73) Assignee: Applied Marketing, Inc., North Olmsted, OH (US)

Reexamination Request:
No. 90/006,772, Sep. 8, 2003

Reexamination Certificate for:
Patent No.: 6,484,720
Issued: Nov. 26, 2002
Appl. No.: 09/692,588
Filed: Oct. 20, 2000

Certificate of Correction issued Feb. 25, 2003.

(51) Int. Cl.
*A62B 9/02* (2006.01)

(52) U.S. Cl. .................................. 128/205.24; 137/535
(58) Field of Classification Search ............ 128/204.26, 128/205.24; 137/501, 505.11, 505.12, 505.18, 137/505.25, 535
See application file for complete search history.

(56) References Cited

U.S. PATENT DOCUMENTS

| | | | | |
|---|---|---|---|---|
| 21,022 A | * | 7/1858 | Powers | 137/248 |
| 310,605 A | * | 1/1885 | Millner | 137/505.11 |
| 714,143 A | * | 11/1902 | Carlson | 137/495 |
| 1,927,669 A | * | 9/1933 | Morrow | 137/505.25 |
| 2,121,312 A | * | 6/1938 | Bicknell | 137/505.12 |
| 3,259,144 A | * | 7/1966 | Taplin | 137/505.41 |
| 3,604,445 A | | 9/1971 | Jordan et al. | 137/113 |
| 4,230,140 A | * | 10/1980 | Hart | 137/81.2 |
| 5,143,116 A | | 9/1992 | Skoglund | 137/487 |
| 5,379,761 A | * | 1/1995 | Schuler | 128/205.24 |
| 5,381,825 A | * | 1/1995 | Garraffa | 137/505.18 |
| 5,487,405 A | * | 1/1996 | Skoglund | 137/501 |
| 5,509,407 A | * | 4/1996 | Schuler | 128/205.24 |
| 5,622,204 A | * | 4/1997 | Skoglund | 137/501 |
| 5,655,524 A | * | 8/1997 | Atkins | 128/205.24 |
| 5,685,297 A | * | 11/1997 | Schuler | 128/205.24 |
| 5,775,368 A | * | 7/1998 | Morino | 137/505.25 |
| 5,899,223 A | | 5/1999 | Shuman, Jr. | 137/505.25 |
| 6,089,259 A | * | 7/2000 | Shuman, Jr. | 137/505.25 |
| 6,158,457 A | * | 12/2000 | Byrd et al. | 137/505.25 |

* cited by examiner

*Primary Examiner*—Aaron J. Lewis

(57) ABSTRACT

An oxygen gas therapy regulator is provided which is small in size and has particularly uniform output characteristics. The regulator uses five springs evenly spaced around a circle concentric with the axis of the regulator piston thereby providing uniform output characteristics.

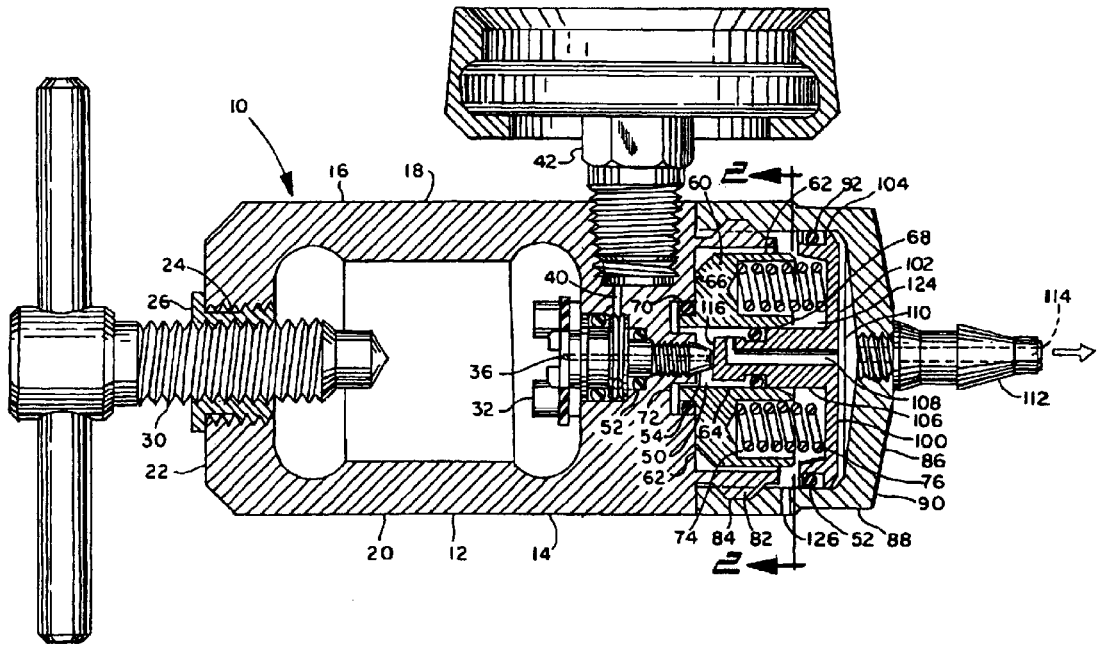

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–10 are cancelled.

* * * * *